United States Patent

Volodin et al.

[11] 4,014,947
[45] Mar. 29, 1977

[54] METHOD OF PRODUCING VINYL CHLORIDE

[76] Inventors: Nikolai Lvovich Volodin, Revoljutsionnaya ulitsa, 7, kv. 12, Sterlitamak; Lev Solomonovich Polak, ulitsa Obrucheva, 18, kv. 22, Moscow; Petr Nikolaevich Endjuskin, ulitsa Druzhby, 68, kv. 14, Sterlitamak; Rafail Izrailevich Levenzon, ulitsa Krasikova, 17, kv. 39; Samuil Markovich Krugly, ulitsa Khlobystova, 6, kv. 14, both of Moscow; Viktor Trofimovich Dyatlov, ulitsa Bljukhera, 2, kv. 78, Sterlitamak, all of U.S.S.R.

[22] Filed: May 27, 1970

[21] Appl. No.: 40,933

[30] Foreign Application Priority Data

June 3, 1969 U.S.S.R. ............................ 1334597
June 3, 1969 U.S.S.R. ............................ 1334593
June 3, 1969 U.S.S.R. ............................ 1334594

[52] U.S. Cl. .................... 260/656 R; 260/654 H; 260/656 AC
[51] Int. Cl.$^2$ ........................................ C07C 21/02
[58] Field of Search ..... 260/679 R, 656 R, 656 AC

[56] References Cited

UNITED STATES PATENTS 3,377,402 4/1968 Sennewald et al. ............... 260/679

FOREIGN PATENTS OR APPLICATIONS 1,068,793 5/1967 United Kingdom ............... 260/656

*Primary Examiner*—James O. Thomas, Jr.
*Assistant Examiner*—A. Siegel

[57] ABSTRACT

A method of producing vinyl chloride, pyrolyzing gaseous and liqud hydrocarbons in a plasma jet of hydrogen or in a mixture of hydrogen and methane, with the addition of chlorine and/or HCl gas in such an amount that the content of HCl gas in the pyrolysis gas thus formed should be equal to the content of acetylene therein. Further the pyrolysis gas containing acetylene and ethylene is quenched with liquid hydrocarbons, purified from higher unsaturated hydrocarbons containing 3 or more carbon atoms, the acetylene is reacted with HCl gas, the resulting vinyl chloride is separated, the ethylene is reacted with chlorine, the dichloroethane thus formed is pyrolyzed with the formation of vinyl chloride and HCl gas, the vinyl chloride is separated, and the HCl gas is recycled to the stage of reacting acetylene and HCl gas.

Said method makes it possible to increase the total yield of acetylene and ethylene at the stage of pyrolysis up to 85%, and the yield of vinyl chloride up to 82% of the initial hydrocarbons used.

1 Claim, 1 Drawing Figure

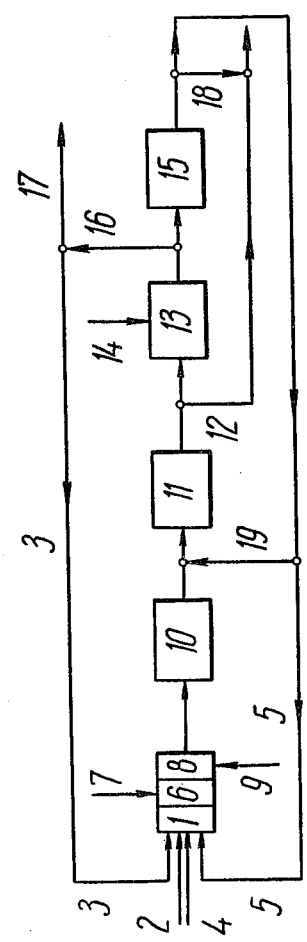

METHOD OF PRODUCING VINYL CHLORIDE

The present invention relates to methods of producing vinyl chloride.

Vinyl chloride is used for synthesizing polyvinyl chloride, which, in turn, is widely employed in the production of plastic materials.

There is known in the art a method of producing vinyl chloride by a process comprising: forming a pyrolysis gas containing acetylene and ethylene by oxidation pyrolysis of liquid hydrocarbons in the presence of water vapour with subsequent quenching of the pyrolysis gas with water; removing higher unsaturated hydrocarbons containing 3 or more carbon atoms from the pyrolysis gas; reacting the acetylene with HCl gas; separating the vinyl chloride thus formed; reacting the ethylene with chlorine and separating the dichloroethane thus formed; thermally decomposing the separated dichloroethane and recycling the HCl gas to the step of reacting acetylene therewith (cf.British Pat. No. 1,068,793).

Also known in the art is a method of producing acetylene and ethylene by pyrolyzing liquid hydrocarbons in a plasma jet of hydrogen, quenching the pyrolysis gas containing acetylene and ethylene with liquid hydrocarbons, removing higher unsaturated hydrocarbons containing 3 or more carbon atoms from the pyrolysis gas, and separating the acetylene and ethylene for their subsequent use in the production of organochlorine compounds, such as vinyl chloride (cf.Federal Republic of Germany Pat. Nos. 1,012,899 and 1,168,419).

Additionally, there is known in the art a process of making acetylene by pyrolyzing methane in a plasma jet of a mixture of hydrogen and methane, quenching the pyrolysis gas containing acetylene, with water, removing the admixtures from the pyrolysis gas, and separating the acetylene (cf. U.S. Pat. No. 3,256,358).

The first of the above-cited methods is disadvantageous in that there is a relatively low yield of acetylene and ethylene (amounting to 48–50%) at the stage of pyrolysis of hydrocarbons, thus resulting in a low yield of vinyl chloride (45–48% of the initial hydrocarbons).

Another disadvantage of the first-mentioned method resides in the use of oxygen and water vapour at the pyrolysis stage, resulting in the formation of by-products.

Still another disadvantage of said first method is that it involves considerable consumption of refrigerants, electric power and solvents for the purification of the pyrolysis gas and separation of the target product due to the presence of considerable amount of impurities and low concentrations of acetylene and ethylene in the pyrolysis gas.

The second and third of the above-cited prior-art methods are disadvantageous in that they require considerable amount of refrigerants, electric power and solvents for purifying the pyrolysis gas and separating acetylene or the mixture of acetylene and ethylene therefrom.

Another disadvantage of the two last-mentioned methods is a high consumption of electric power in the course of pyrolyzing the hydrocarbons.

It is an object of the present invention to provide such a method of producing vinyl chloride, which would make it possible to increase the yield of acetylene and ethylene at the stage of pyrolysis of hydrocarbons, and, thereby, the yield of the target product.

Another object of the invention is to provide such a method of producing vinyl chloride, which would obviate the use of oxygen and water vapour in the pyrolysis of hydrocarbons, and thus preclude the formation of oxygen-containing by-products.

It is also an object of the invention to reduce the amount of refrigerants, electric power and solvents required for the purification of the pyrolysis gas and separation of the target product, high consumption thereof in the prior-art methods being associated with the presence of large amounts of admixtures and with low concentrations of acetylene and ethylene in the pyrolysis gas.

Still another object of the invention is to provide such a method of producing vinyl chloride, which would allow a reduction in the consumption of electric power for carrying out the pyrolysis of hydrocarbons.

In accordance with the said and other objects, the present invention resides in that gaseous and liquid hydrocarbons are pyrolyzed in a plasma jet of hydrogen or of a mixture of hydrogen and methane with the addition of chlorine and/or HCl gas in a quantity such that the content of the HCl gas in the pyrolysis gas formed should be equal to the content of acetylene in the pyrolysis gas, the pyrolysis gas containing acetylene and ethylene being then quenched with liquid hydrocarbons; in that higher unsaturated hydrocarbons containing 3 or more carbon atoms are then removed from the pyrolysis gas; the acetylene is reacted with the HCl gas. and the vinyl chloride thus formed is separated; the ethylene is reacted with chlorine and the dichloroethane thus formed is pyrolyzed with the formation of vinyl chloride and HCl gas; the vinyl chloride thus formed is separated and the HCl gas is recycled and used to be reacted with acetylene at the respective stage. Thus, the reaction follows the scheme:

1. Hydrocarbons + Cl$_2$ + HCl (optional)  HCl + CH CH + CH$_2$ = CH$_2$ + higher unsaturated hydrocarbons
2. quench with liquid hydrocarbons and remove higher unsaturated hydrocarbons

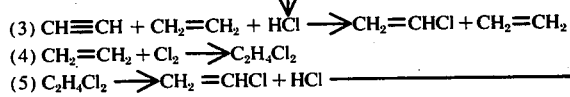

(3) CH≡CH + CH$_2$=CH$_2$ + HCl —>CH$_2$=CHCl + CH$_2$=CH$_2$
(4) CH$_2$=CH$_2$ + Cl$_2$ —>C$_2$H$_4$Cl$_2$
(5) C$_2$H$_4$Cl$_2$ —>CH$_2$=CHCl + HCl ——

Carrying out the pyrolysis under the above-stated conditions allows an increase of the total yield of acetylene and ethylene up to 85%, and the yield of the target product up to 82%, as estimated for the initial hydrocarbons, with the use of oxygen and water vapour during the pyrolysis being obviated, whereby it becomes possible to preclude the formation of oxygen-containing by-products, to reduce the consumption of electric power and solvents required for the removal of admixtures from the pyrolysis gas and for the separation of the target product, to diminish the consumption of electric power for carrying out the pyrolysis through the utilization of heat evolving in the course of the reaction of formation of the HCl gas from chlorine and hydrogen during the pyrolysis (in case of using chlorine in the plasma jet).

It is expedient, that the HCl gas recycled to the stage of reacting it with acetylene should be used as a plasmaforming gas. This allows the dilution of the reagents with a gas that is inert in the given process, viz., with hydrogen to be obviated.

The present method will become more fully apparent from the following description in conjunction with the accompanying drawing which is a diagrammatic presentation of the flow sheet of the herein-proposed process of producing vinyl chloride.

A plasmotron or plasma jet generator is fed with hydrogen or with a mixture of hydrogen and methane, and also with chlorine and/or HCl gas. Said hydrogen or mixture of hydrogen and methane can be fed to the plasmotron via a pipeline 2 (from the outside). Besides, the mixture of hydrogen and methane can be fed to the plasmotron via a pipeline 3, recycling said mixture from the stage of reacting ethylene with chlorine. Chlorine and HCl gas can be supplied to the plasmotron via a pipeline 4 (from the outside). HCl gas can be fed to the plasmotron via a pipeline 5, by recycling it from the stage of pyrolysis of dichloroethane, as discussed in greater detail hereinbelow.

The mixture of gases, while passing through the field of the electric arc of the plasmotron, becomes heated up to an average mass temperature of 2000°–6000° C and enters a pyrolysis reactor 6, whereto initial hydrocarbons are fed via a pipeline 7. The stock fed to the reactor 6 can be composed of gaseous or liquid hydrocarbons, such as ethane, propane, butane, gasoline, kerosene, gas oil, petroleum, and the like. The hydrocarbon stock prior to being fed to the reactor 6, and the heat carriers (hydrogen, the mixture of hydrogen and methane, chlorine and HCl gas) prior to being admitted to the plasmotron 1, can be preheated with a view to saving the electric power and increasing the concentration of acetylene and ethylene in the pyrolysis gas. This pyrolysis gas formed during the pyrolysis of the hydrocarbon stock in the reactor 6 is fed to a quenching chamber 8, where it is cooled by being mixed with a stream of liquid hydrocarbons incoming via a pipeline 9. The cooled pyrolysis gas which contains 13–20 vol.% of acetylene, 13–20 vol.% of HCl gas, 13–6 vol.% of ethylene, 49–47 vol.% of hydrogen, 10–6 vol.% of methane, and 2–1 vol.% of higher unsaturated hydrocarbons containing 3 or more carbon atoms is sent to an apparatus 10 to be purified from said hydrocarbons containing 3 or more carbon atoms. The purification stage is effected by conventional methods, such as absorption. The purified pyrolysis gas is fed to a reactor 11, where the acetylene and the HCl gas contained in the pyrolysis gas are reacted with the formation of vinyl chloride. The vinyl chloride thus formed is absorbed or condensed from the pyrolysis gas, or, else, is separated by rectification under pressure, and then is discharged through a pipeline 12 into a collector (not shown). The mixture of gases remaining after the separation of the vinyl chloride and consisting of ethylene, methane and hydrogen is fed to a reactor 13 where the ethylene is reacted with chlorine, gaseous chlorine being fed to said reactor 13 through a pipeline 14. Liquid dichloroethane formed by the reaction between the ethylene and chlorine is fed to a reactor 15 to be pyrolyzed, and the residual gases resulting after the chlorination stage, which are a mixture of hydrogen and methane, are discharged from the reactor 13 through a pipeline 16. A portion of the residual gases via the pipeline 3 is returned to the plasmotron 1, and the rest of the residual gases is transferred via a pipeline 17 and used as a fuel in the processes of pyrolyzing the dichloroethane and preheating the stock hydrocarbons, or for producing commercial hydrogen.

The vinyl chloride formed by the pyrolysis of the dichloroethane is separated from the HCl gas, for example, by absorption, condensation, or rectification techniques, and discharged from the reactor 15 via a pipeline 18, and the HCl gas is recycled to be reacted with acetylene, via a pipeline 19 or the pipeline 5 (in the latter case the HCl gas is used also as a plasmaforming gas).

For a better understanding of the present invention, given hereinbelow are illustrative examples of producing vinyl chloride in accordance with the method of the invention.

EXAMPLE 1

Vinyl chloride was produced in accordance with the flow sheet described hereinabove.

The plasmotron 1 was fed with a mixture of gases comprising 82 vol.% of hydrogen and 18 vol.% of methane, recycled from the stage of chlorination of ethylene, at a rate of 5.3 nm$^3$ per hour, with HCl gas recycled from the stage of pyrolysis of dichloroethane, at a rate of 1.3 nm$^3$ per hour, and with gaseous chlorine, at a rate of 0.88 nm$^3$ per hour. The mixture of gases was heated while passing through the electric arc of the plasmotron and fed to the pyrolysis reactor 6. The useful power of the plasmotron was 20 kW. The pyrolysis reactor, besides the above-stated mixture of gases, was also fed with vapours of petrol having a temperature of 200° C, at a rate of 7.2 kg per hour. The pyrolysis temperature was about 1350° C. The reaction products were cooled by supplying petrol into the quenching chamber 8. After the separation from the liquid phase, the composition of the pyrolysis gas was as follows (in vol.%): hydrogen, 46.8; methane, 10.0; ethylene, 8.0; HCl gas, 17.0; acetylene, 17.0; unsaturated hydrocarbons containing 3 and more carbon atoms, 1.0.

The amount of the pyrolysis gas was 18 nm$^3$ per hour. The degree of conversion of the hydrocarbon stock to gaseous products was 95%. The total yield of acetylene and ethylene was 80%.

After being quenched, the pyrolysis gas was purified in the apparatus 10 from higher unsaturated hydrocarbons by absorption with kerosene at a temperature of −15° C and a pressure of 9 abs. atm., and then fed into the reactor 11 for the acetylene to be reacted with HCl gas. The reaction between the acetylene and the HCl gas contained in the pyrolysis gas was carried out under the following conditions: the temperature of the reaction mixture was 160° C, pressure, 9 abs. atm., the catalyst was mercuric chloride applied onto granules of active carbon. On leaving the reactor 11 the gas had the following composition (in vol.%): vinyl chloride, 20.7; hydrogen, 57.2; methane, 12.2; ethylene, 9.7; acetylene, 0.2. The vinyl chloride was separated from the pyrolysis gas by absorption with cooled dichloroethane. The amount of the vinyl chloride thus separated was 8.5 kg per hour, the yield being 98% of the acetylene. The residual gases remaining after the separation of the vinyl chloride, that consisted of 72.3 vol.% of hydrogen, 12.2 vol.% of ethylene, 15.3 vol.% of methane and 0.2 vol.% of acetylene, were fed into the reactor 13 for the ethylene to be reacted with chlorine, gaseous chlorine being fed thereinto at a rate of 1.4 nm³ per hour. The ethylene was chlorinated on a ferric chloride catalyst at a temperature of 30° C. The resulting liquid dichloroethane (its yield being 97% of the ethylene) was purified from admixtures by rectification and pyrolyzed in the reactor 15. The vinyl chloride formed during the pyrolysis was separated from the HCl gas by absorption with dichloroethane. The amount of the separated vinyl chloride was 3.7 kg per hour, the yield was 96% of the dichloroethane.

A portion of the residual gases (5.3 nm³ per hour), consisting of 82 vol.% of hydrogen and 18 vol.% of methane, without taking into account insignificant admixtures of other hydrocarbons and HCl gas, was recycled to the plasmotron 1 from the stage of chlorination of the ethylene. The HCl gas resulting during the pyrolysis of the dichloroethane was also recycled to the plasmotron at a rate of 1.3 nm³ per hour.

The yield of the vinyl chloride was 74% of the petrol taken and 96% of the chlorine.

EXAMPLE 2

Fed to the plasmotron 1 was a mixture of gases, consisting of 85 vol.% of hydrogen and 15 vol.% of methane, which was recycled from the stage of reacting ethylene with chlorine, at a rate of 5.6 nm³ per hour, and HCl gas, recycled from the stage of the pyrolysis of dichloroethane, at a rate of 2.04 nm³ per hour. This mixture of gases, while passing through the electric arc of the plasmotron, was heated and then fed into the pyrolysis reactor 6. The useful power of the plasmotron was 20 kW. Besides the above-specified gases, the pyrolysis reactor was also fed with butane at a rate of 7.2 kg per hour. The temperature of the pyrolysis was about 1100° C. The reaction products were cooled in the quenching chamber 8 by feeding naphthalene thereinto. After the separation from the liquid phase, the pyrolysis gas had the following composition (in vol.%): hydrogen, 49.9; methane, 10.8; ethylene, 13.0; HCl gas, 12.0; acetylene, 12.2; unsaturated hydrocarbons containing 3 and more carbon atoms, 2.1.

The amount of the pyrolysis gas produced was 17 nm³ per hour. The degree of conversion of the stock hydrocarbons to gaseous products was 92%. The total yield of acetylene and ethylene was 72%.

After being quenched, the pyrolysis gas was purified in the apparatus 10 from higher unsaturated hydrocarbons by absorption with kerosene at a temperature of −20° C and under a pressure of 8 abs.atm., and then fed to the reactor 11 for the acetylene to be reacted with HCl gas, said reactor 11 containing a mercuric chloride catalyst applied onto granules of active carbon. The reaction was carried out at a temperature of 180° C and under a pressure of 8 abs.atm. Upon leaving the reactor 11, the gas had the following composition (in vol.%): vinyl chloride, 14.0; hydrogen, 58.1; methane, 12.6; ethylene, 15.0; acetylene, 0.3. The vinyl chloride was separated from the pyrolysis gas by rectification under a pressure of 8 abs.atm. The amount of the vinyl chloride thus separated was 5.6 kg per hour, the yield was 98% of the acetylene. The residual gases after the separation of the vinyl chloride, which consisted of 67.7 vol.% of hydrogen, 17.4 vol.% of ethylene, 14.6 vol.% of methane and 0.3 vol.% of acetylene, were fed into the reactor 13 for the ethylene to be reacted with chlorine, gaseous chlorine being also fed thereinto at a rate of 2.17 nm³ per hour. The ethylene was chlorinated on a ferric chloride catalyst at a temperature of 50° C. The resulting liquid dichloroethane (its yield being 97% of the ethylene) was pyrolyzed in the reactor 15. The vinyl chloride formed during the pyrolysis was separated from the HCl gas by condensation. The amount of the vinyl chloride thus separated was 5.7 kg per hour, its yield being 96% of the dichloroethane.

A portion of the residual gases (5.6 nm³ per hour) was recycled from the chlorination stage to the plasmotron 1. These residual gases consisted of 85 vol.% of hydrogen and 15 vol.% of metane, not taking into account an insignificant amount of admixtures. The HCl gas resulting during the pyrolysis of the dichloroethane was, in an amount of 2.04 nm³ per hour, also recycled into the plasmotron.

The yield of the vinyl chloride was 70% of the butane fed and 93% of the chlorine.

EXAMPLE 3

Fed to the plasmotron 1 was hydrogen at a rate of 3.25 nm³ per hour and chlorine at a rate of 0.75 nm³ per hour. The mixture of hydrogen and chlorine, while passing through the electric arc of the plasmotron, was heated, and then fed to the pyrolysis reactor 6. The useful power of the plasmotron was 12 kW. Into the pyrolysis reactor, besides the above-said gases, kerosene was also fed at a rate of 3.9 kg per hour. The temperature of the pyrolysis was 1400° C. The reaction products were cooled in the quenching chamber 8 by feeding kerosene thereinto. After the separation from the liquid phase, the pyrolysis gas had the following composition (in vol.%): hydrogen, 51.0; methane, 8.0; ethylene, 5.0; acetylene, 20.3; HCl gas, 15.0; unsaturated hydrocarbons containing 3 and more carbon atoms, 0.3.

The amount of the pyrolysis gas was 10 nm³ per hour. The degree of conversion of the stock hydrocarbons to gaseous products was 98%. The total yield of the acetylene and ethylene was 76%.

After quenching, the pyrolysis gas was purified in the apparatus 10 from higher unsaturated hydrocarbons by absorption with kerosene at a temperature of −15° C and under a pressure of 9 abs.atm., and then mixed with the HCl gas recycled from the stage of pyrolysis of dichloroethane at a rate of 0.5 nm³ per hour. Then the mixture of the pyrolysis gas and the HCl gas was fed to the reactor 11 for reacting acetylene with the HCl gas. The conditions of the process of reacting the acetylene with the HCl gas were the same as in Example 1. The gas upon leaving the reactor 11 had the following composition (in vol.%): vinyl chloride, 23.8; hydrogen, 60.5; methane, 9.4; ethylene, 6.0; acetylene, 0.3. The vinyl chloride was separated from the pyrolysis gas by absorption with cooled dichloroethane. The amount of the separated vinyl chloride was 5.5 kg per hour, the yield was 98% of the acetylene. The residual gases after the separation of the vinyl chloride, consisting of 79.8 vol.% of hydrogen, 7.6 vol.% of ethylene, 12.2 vol.% of methane, and 0.4 vol.% of acetylene, were fed into the reactor 13 for reacting the ethylene with chlorine, gaseous chlorine being fed into said reactor at a rate of 0.51 nm³ per hour. The resulting liquid dichloroethane (its yield being 97% of the ethylene) was purified from admixtures by rectification and pyrolyzed in the reactor 15.

The vinyl chloride formed during the pyrolysis was separated from the HCl gas by absorption with dichloroethane. The amount of the separated vinyl chloride was 1.3 kg per hour, the yield thereof was 96% of the dichloroethane.

The HCl gas resulting during the pyrolysis of the dichloroethane was recycled into the reactor 11 for reacting the acetylene with the HCl gas, at a rate of 0.5 nm$^3$ per hour.

The yield of the vinyl chloride was 75% of the kerosene fed and 97% of the chlorine.

What is claimed is:

1. A method of producing vinyl chloride, comprising forming a plasma jet of gases consisting essentially of (A) a member selected from the group consisting of hydrogen and a mixture of hydrogen and methane, and (B) a plasma-forming gas selected from the group consisting of chlorine, HCl gas and a mixture of chlorine and HCl gas; pyrolyzing gaseous and liquid hydrocarbons in said plasma jet of gases to form a pyrolysis gas of acetylene, ethylene, HCl gas and higher unsaturated hydrocarbons, the plasma-forming gas being added in such an amount that the content of the HCl gas in the pyrolysis gas is equal to the content of the acetylene in said pyrolysis gas; quenching said pyorlysis gas with liquid hydrocarbons; removing said higher unsaturated hydrocarbons containing at least 3 carbon atoms from said pyrolysis gas; reacting the acetylene with HCl gas to form vinyl chloride; separating the vinyl chloride; reacting the ethylene with chlorine to form dichloroethane; pyrolyzing the dichloroethane to form vinyl chloride and HCl gas; separating said vinyl chloride from said HCl gas; and recycling said HCl gas to the stage of forming said plasma jet.

* * * * *